United States Patent
Wu et al.

(10) Patent No.: US 9,440,981 B2
(45) Date of Patent: Sep. 13, 2016

(54) PYRROLO[2, 1-F] [1,2,4]TRIAZINE DERIVATIVE AND USE THEREOF FOR TREATING TUMORS

(71) Applicant: PHARMABLOCK (NANJING) R&D CO. LTD., Jiangsu (CN)

(72) Inventors: Xihan Wu, Jiangsu (CN); Minmin Yang, Jiangsu (CN); Qingning Shu, Jiangsu (CN); Chunrui Zhu, Jiangsu (CN)

(73) Assignee: PHARMABLOCK (NANJING) R&D CO. LTD, Nanjing (CN)

( * ) Notice: Subject to any disclaimer, the term of this patent is extended or adjusted under 35 U.S.C. 154(b) by 19 days.

(21) Appl. No.: 14/404,217

(22) PCT Filed: May 17, 2013

(86) PCT No.: PCT/CN2013/075796
§ 371 (c)(1),
(2) Date: Nov. 26, 2014

(87) PCT Pub. No.: WO2013/178021
PCT Pub. Date: Dec. 5, 2013

(65) Prior Publication Data
US 2016/0115166 A1    Apr. 28, 2016

(30) Foreign Application Priority Data
Jun. 1, 2012 (CN) .......................... 2012 1 0178854

(51) Int. Cl.
*C07D 487/04* (2006.01)
*A61K 31/5377* (2006.01)
*C07D 519/00* (2006.01)

(52) U.S. Cl.
CPC ......... *C07D 487/04* (2013.01); *A61K 31/5377* (2013.01); *C07D 519/00* (2013.01)

(58) Field of Classification Search
CPC ..................................................... C07D 487/04
See application file for complete search history.

(56) References Cited

FOREIGN PATENT DOCUMENTS

| CN | 102675323 A | 9/2012 |
|---|---|---|
| EP | 2 524 918 A1 | 11/2012 |
| WO | 2010/119264 A1 | 10/2010 |
| WO | 2011/089400 A1 | 7/2011 |

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*

* cited by examiner

*Primary Examiner* — Rebecca Anderson
(74) *Attorney, Agent, or Firm* — Ladas & Parry LLP

(57) ABSTRACT

Disclosed are a pyrrolo[2,1-f][1,2,4]triazine derivative of Formula (I) and use thereof for treating tumors. The compound has remarkable antiproliferative activity for a variety of human tumor cell lines, and is useful for treating cancers, especially solid tumors such as gastric cancer, lung cancer, liver cancer, breast cancer, colon cancer, prostatic cancer, and oral cancer.

9 Claims, No Drawings

PYRROLO[2, 1-F] [1,2,4]TRIAZINE DERIVATIVE AND USE THEREOF FOR TREATING TUMORS

RELATED APPLICATION

This application is a national phase entry under 35 USC 371 of International Patent Application No PCT/CN2013/075796 filed on 17 May 2013, which was published on 5 Dec. 2013 with International Publication Number WO 2013/178021 A1, which claims priority from Chinese Patent Application No. 201210178854.X filed on 1 Jun. 2012.

BACKGROUND OF THE INVENTION

1. Field of the Invention

The present invention relates to the field of medicinal chemistry, and more particularly to a pyrrolo[2,1-f][1,2,4]triazine derivative and use thereof for treating tumors.

2. Description of Related Art

With the changes in living environment, standard, and style of human and the progressions in medical science, significant changes occur in disease spectrum. General infectious diseases are gradually controlled, but malignant tumors become one of the primary diseases that are increasingly common and seriously threaten the life and quality of life of human. At present, cancers are the second leading cause of death in China and even in the whole world. Recently, the nature of tumors is constantly elucidated with the advancement in molecular oncology and molecular pharmacology. Malignant tumors are diseases in which the proliferation and spread of the cells in the organisms are out of control, and thus are disease characterized by abnormal cell proliferation and differentiation. The therapies for tumors include surgical resection, radiotherapy, and chemotherapy with antitumor drugs. The efficacy of these treatment approaches depends on the type and the stage of the tumor development. Generally, the chemotherapeutic agent, as a main treatment approach, is only suitable for several tumors, for example, leukemia and lymphatic system cancers, but as an adjuvant treatment for surgery or radiotherapy, is suitable for various types of tumors. Recently, the development of the anti-tumor drugs progresses rapidly and now to a new stage. Presently, the focus in development of the anti-tumor drugs has changed from traditional cytotoxic agents with low selectivity and high toxicity to new anti-tumor drugs with high potency, low toxicity, and high specificity and selectively targeting critical enzymes involved in cell signaling pathways associated with differentiation and proliferation of tumor cells.

SUMMARY OF THE INVENTION

The present invention discloses a pyrrolo[1,2-f][1,2,4]triazine derivative of Formula (I), which has excellent anti-tumor effect as indicated by pharmacological test.

According to the present invention, the structural Formula (I) of the pyrrolo[2,1-f][1,2,4-]triazine is as shown below:

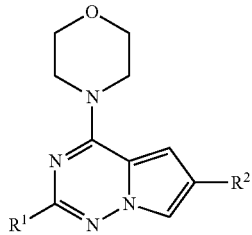

in which R¹ represents indolyl, indazolyl, azaindolyl, or aminopyrimidinyl;

R² represents

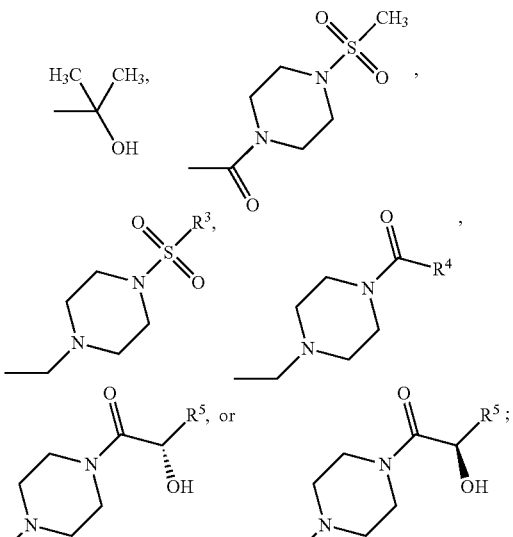

R³ represents C1-C6 alkyl, R⁴ represents C1-C6 alkyl, and R⁵ represents C1-C6 alkyl;

R¹ preferably represents:

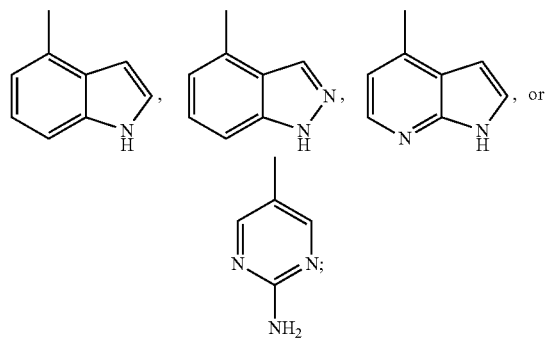

R³ preferably represents methyl or ethyl;
R⁴ preferably represents methyl or cyclopropyl; and
R⁵ preferably represents methyl.

Preferred are some compounds having a structural formula below:

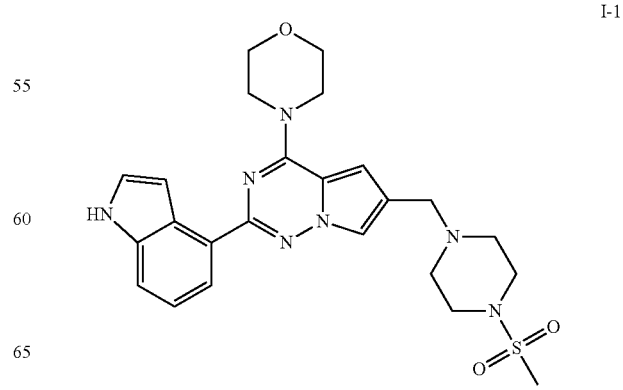

I-1

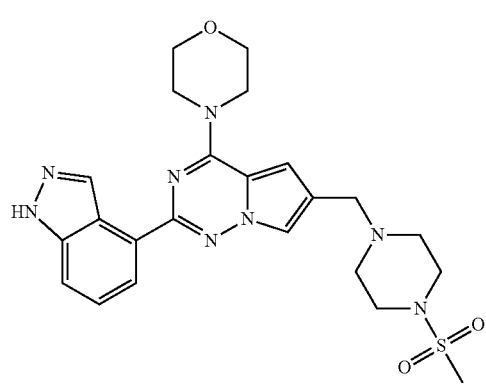
I-2
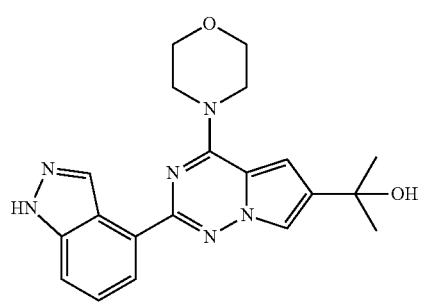
I-6
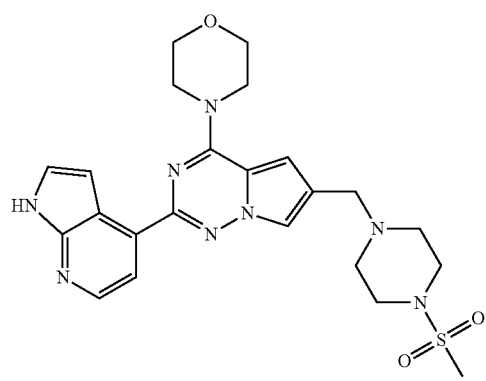
I-3
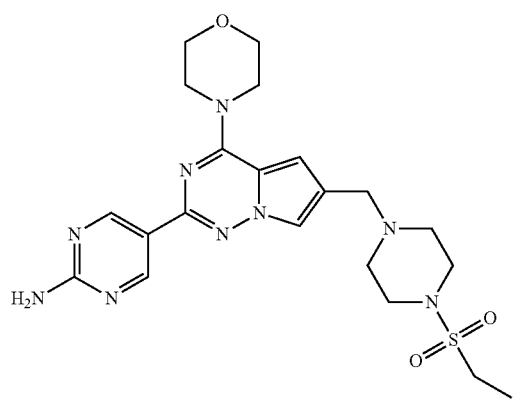
I-7
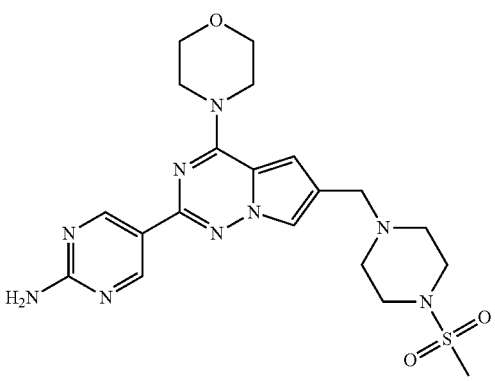
I-4
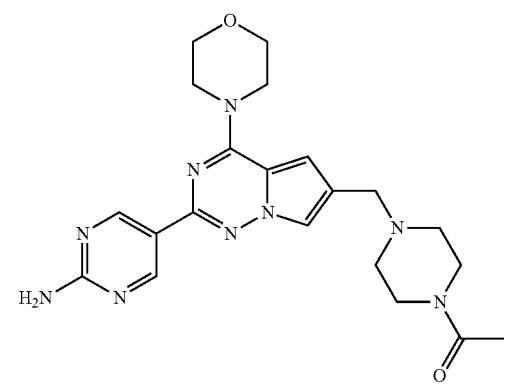
I-8
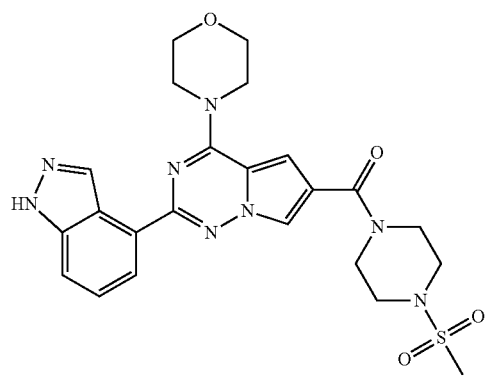
I-5
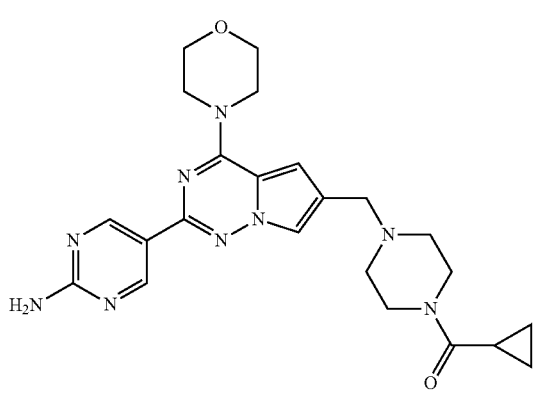
I-9

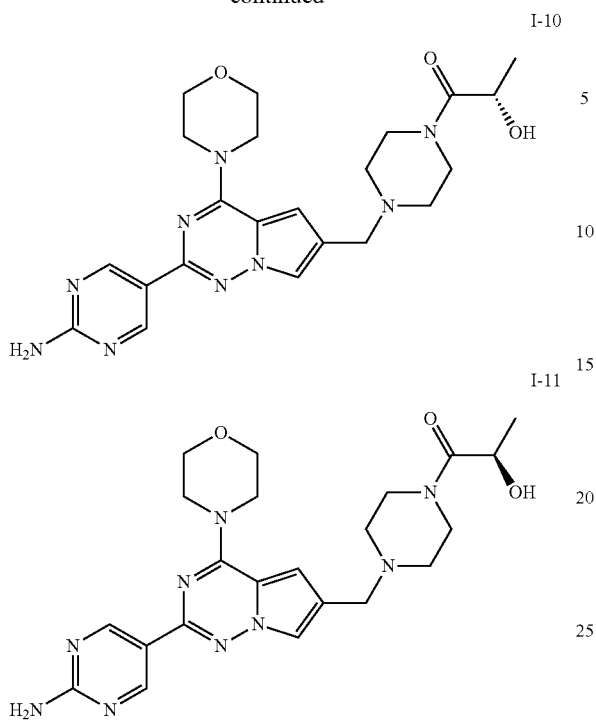

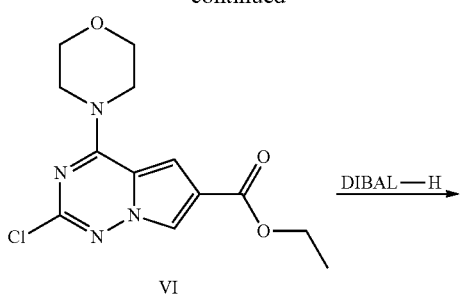

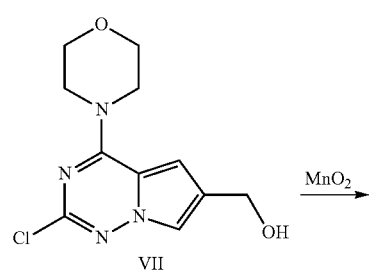

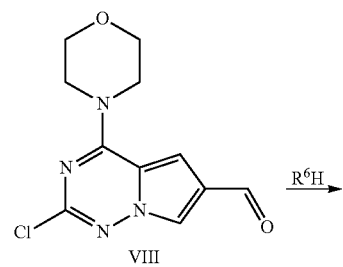

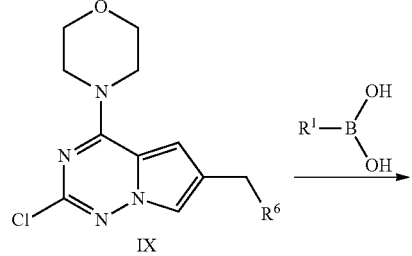

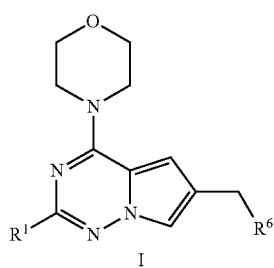

The compound of Formula (I) according to the present invention may form a salt with a pharmaceutically acceptable acid. The pharmaceutically acceptable salt may be in the form of a salt with an organic or inorganic acid, for example, hydrochloric acid, sulfuric acid, phosphoric acid, maleic acid, fumaric acid, citric acid, methanesulfonic acid, p-toluene sulfonic acid, or tartaric acid, and other acids that are known to be pharmaceutically acceptable.

Some compounds of the present invention may be prepared by a process below.

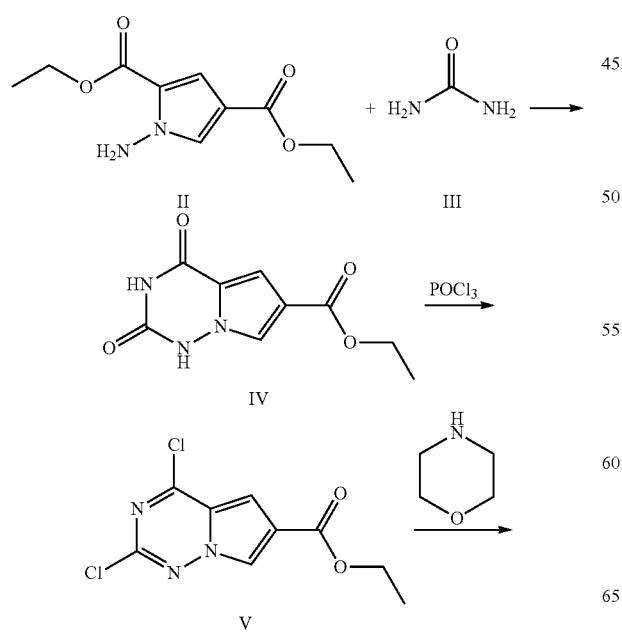

In the compound of Formula (I), $R^1$ preferably represents:

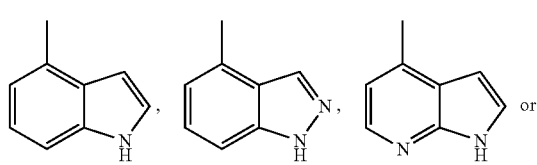

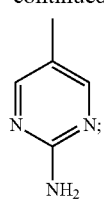
and
R⁶ preferably represents:
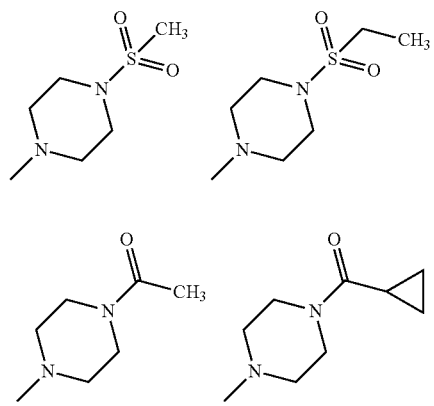
Compound 1-5 is synthesized through a route below:
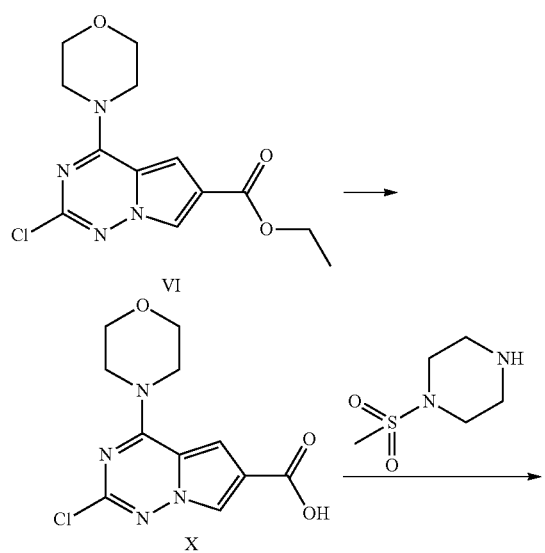
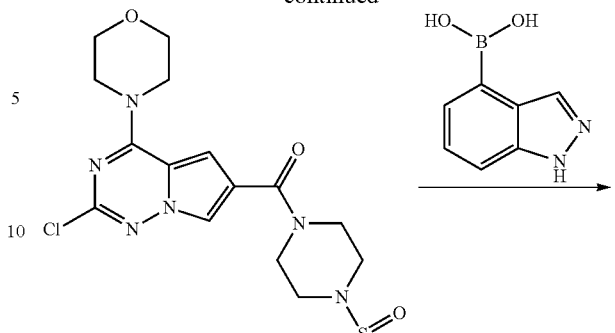
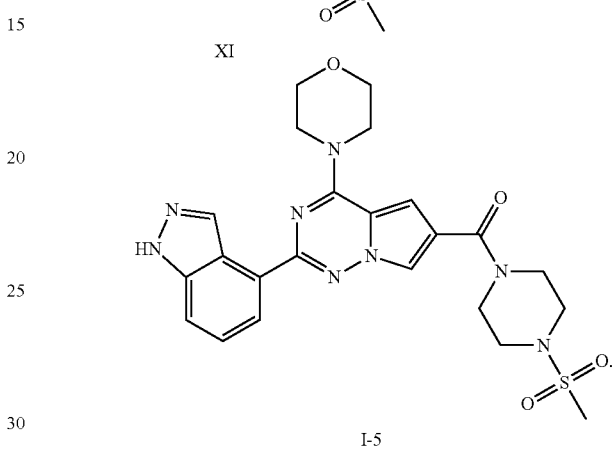
I-5
Compound 1-6 is synthesized through a route below:
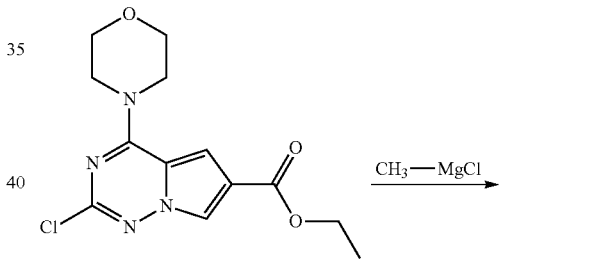
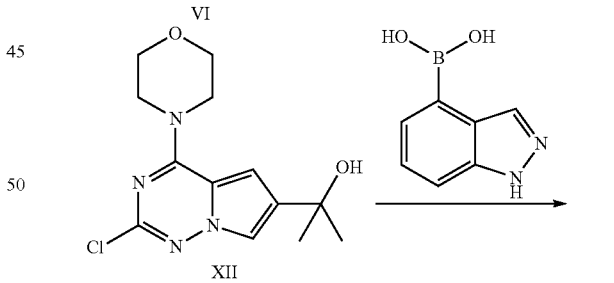
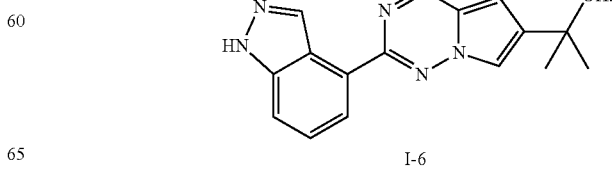
I-6

In clinic, the compound of the present invention is dosed through oral administration, injection, or other routes.

In clinic, the compound of the present invention is administered at a dosage of 0.01-1000 mg/day, or at a dosage falling outside this range depending on the severity of the disease or different dosage forms.

As shown by pharmacological test, the compound of the present invention has excellent anti-tumor activity with an $IC_{50}$ ranging from 0.03 to 12.6 μM. Accordingly, the compound of the present invention is useful in preparation of drugs for treating tumors. Pharmacodynamic tests of some compounds of the present invention and results therefrom are given hereinafter.

The inhibition of the compounds of the present invention on growth of a variety of human tumor cell lines is evaluated by MTT assay.

Method: cells in exponential phase (human gastric cancer cell line SGC-7901, human non-small cell lung cancer cell line A549, human breast cancer cell line BT-549, human prostatic cancer cell line PC-3, human colon cancer cell line HT-29, and human liver cancer cell line SMMC-7721) are seeded at a density of $1.5 \times 10^4$ in a 96-well plate. After 24-hr culture, the cells are grown to confluent and the previous culture medium is aspirated. The test includes a control group, and a treatment group. In the control group, a 1640 medium containing 10% fetal bovine serum is replenished; and in the treatment group, a medium containing 100 μM, 50 μM, 10 μM, 1 μM, 0.1 μM, 0.01 μM, 0.001 μM, 0.0001 μM, and 0.00001 μM test compound is replenished. After 96-hr culture, 5 mg/mL MTT is added, and cultured in a $CO_2$ incubator for another 4 hrs. Then, 100 μL of the supernatant is aspirated from the upper portion of the culture medium, and placed in the dark for 10 min after 100 μL DMSO is added. The absorbance (at 570 nm) is measured on a microplate reader (available from Sunrise Co., Ltd.), and the cell viability is calculated from the absorbance. 6 replicate wells are set for each treatment. Cell viability (%)=$\Delta OD_{treatment}/\Delta OD_{control} \times 100$.

The $ID_{50}$ values of six compounds for inhibiting the growth of numerous human tumor cell lines are calculated by Sigmaplot 10.0 software and are shown in Table 1.

activity for a variety of human tumor cell lines, and are useful for treating cancers, and especially solid tumors such as gastric cancer, lung cancer, liver cancer, breast cancer, colon cancer, prostatic cancer, and oral cancer.

DETAILED DESCRIPTION OF THE INVENTION

Example 1

Synthesis of Compound IV

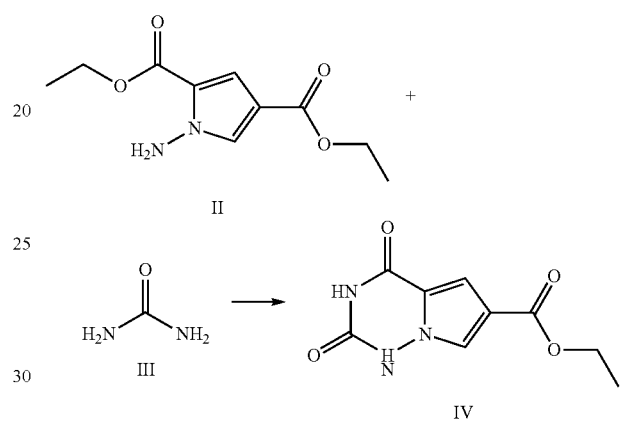

To Compound II (1.1 g, 4.8 mmol), urea (Compound III) (2.4 g, 43 mmol) was added, heated to 180° C., and reacted for 2 hrs. Then, the reaction solution was cooled to room temperature, and 30 mL water was added and continuously stirred, to dissolve most of the solid. The undissolved solid was filtered out, and the filtrate was spun to dryness, to obtain 1.43 g of Compound IV as a brown solid. Yield 70%. $^1$H NMR (400 MHz, DMSO-$d_6$) δ (ppm) 7.35 (d, J=1.9 Hz,

TABLE 1

$IC_{50}$ values of the compounds of the present invention for numerous human tumor cell lines

| Compound | $IC_{50} \pm SD$ (μM) | | | | | |
|---|---|---|---|---|---|---|
| | PC-3 | A549 | HT-29 | BT-549 | SGC-7901 | SMMC-7721 |
| I-1 | 0.51 ± 0.06 | 2.61 ± 0.34 | 0.99 ± 0.04 | 1.27 ± 0.08 | 2.15 ± 0.14 | 1.69 ± 0.18 |
| I-2 | 0.44 ± 0.08 | 2.95 ± 0.45 | 0.16 ± 0.03 | 0.35 ± 0.15 | 1.35 ± 0.28 | 2.53 ± 1.49 |
| I-3 | 0.78 ± 0.36 | 2.73 ± 0.52 | 0.96 ± 0.31 | 1.99 ± 0.07 | 2.52 ± 0.06 | 1.72 ± 0.07 |
| I-4 | 1.17 ± 0.14 | 0.62 ± 0.06 | 1.21 ± 0.04 | 0.61 ± 0.07 | 0.83 ± 0.03 | 0.63 ± 0.11 |
| I-5 | 0.22 ± 0.01 | 1.96 ± 0.33 | 0.73 ± 0.02 | 0.59 ± 0.22 | 3.35 ± 0.46 | 2.15 ± 0.19 |
| I-6 | 1.05 ± 0.64 | 1.35 ± 0.28 | 2.15 ± 0.19 | 2.6 ± 0.67 | 1.01 ± 0.02 | 1.84 ± 0.32 |
| I-7 | 0.29 ± 0.13 | 1.93 ± 0.23 | 0.47 ± 0.09 | 0.34 ± 0.04 | 2.39 ± 0.48 | 1.63 ± 0.39 |
| I-8 | 0.14 ± 0.09 | 1.03 ± 0.14 | 0.29 ± 0.05 | 0.11 ± 0.02 | 1.42 ± 0.23 | 1.28 ± 0.23 |
| I-9 | 0.93 ± 0.18 | 3.21 ± 0.38 | 0.87 ± 0.16 | 0.41 ± 0.11 | 2.51 ± 0.35 | 3.14 ± 0.38 |
| I-10 | 0.20 ± 0.11 | 1.48 ± 0.19 | 0.31 ± 0.08 | 0.13 ± 0.03 | 1.29 ± 0.14 | 1.05 ± 0.24 |
| I-11 | 0.25 ± 0.12 | 1.50 ± 0.20 | 0.85 ± 0.18 | 0.29 ± 0.13 | 1.49 ± 0.15 | 2.05 ± 0.28 |
| GDC-0941 | 0.22 ± 0.02 | 1.98 ± 0.34 | 0.78 ± 0.02 | 0.59 ± 0.22 | 9.37 ± 1.43 | 2.45 ± 0.19 |

The results from the above test show that the compounds of the present invention have remarkable anti-proliferative 1H), 6.82 (d, J=1.9 Hz, 1H), 4.18 (q, 2H), 1.25 (t, 3H); MS Found $(M+H)^+$=214.1.

Synthesis of Compound V

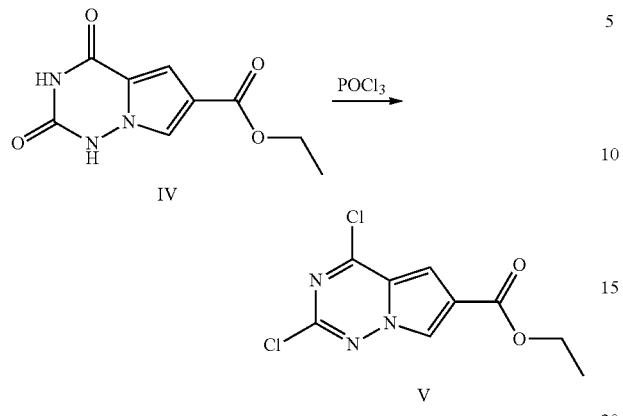

To Compound IV (3.2 g, 0.02 mol), 50 mL phosphorus oxychloride (POCl$_3$) and 10 mL N,N-diisopropylethyl amine (DIPEA) were added and reacted at 130° C. for 10 hrs. Then, the reaction solution was cooled to room temperature, poured into iced water, and extracted with dichloromethane (DCM). The organic phase was washed with saturated aqueous NaCl solution, dried over anhydrous Na$_2$SO$_4$, and purified by column chromatography eluting with petroleum (PE)/ethyl acetate (EA), to obtain 2.26 g of Compound V as a light yellow solid. Yield 65.8%. $^1$H NMR (400 MHz, CDCl$_3$) δ (ppm) 8.27 (d, J=0.9 Hz, 1H), 7.49 (d, J=0.9 Hz, 1H), 4.41 (q, 2H), 1.42 (t, 3H); MS Found (M+H)$^+$=261.3.

Synthesis of Compound VI

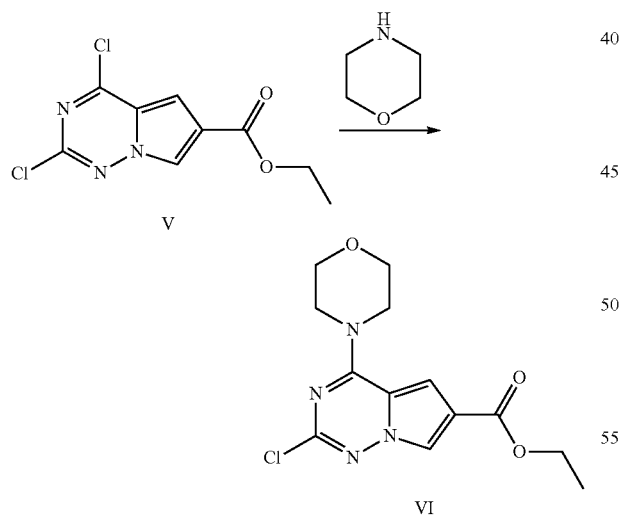

To Compound V (1.1 g, 5.8 mmol), 60 mL methanol (MeOH) was added, and then morpholine (2.0 g, 0.023 mol) was added and reacted for 30 min. The reaction solution was spun to dryness and purified by column chromatography (PE/EA), to obtain 0.96 g of Compound VI as a light yellow solid. Yield 82%. $^1$H NMR (400 MHz, CDCl$_3$) δ (ppm) 8.32 (d, J=0.9 Hz, 1H), 7.28 (d, J=0.9H, 1H), 4.3 (q, 2H), 4.03 (m, 4H), 3.89 (m, 4H), 1.32 (t, 3H); MS Found (M+H)$^+$=311.5.

Synthesis of Compound VII

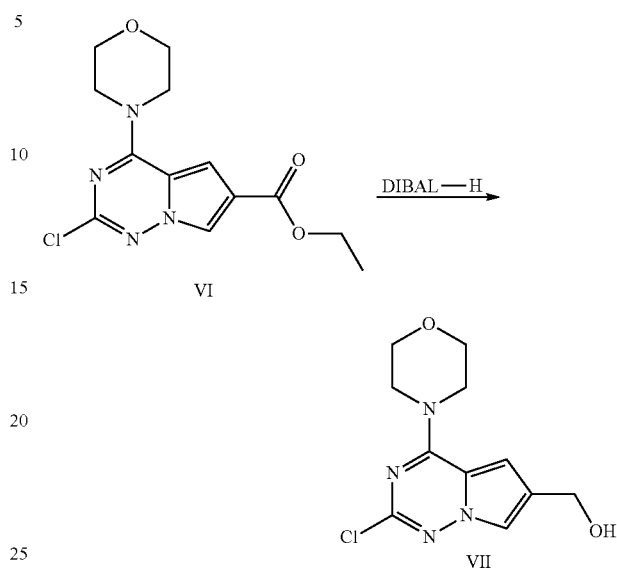

To Compound VI (42 mg, 0.14 mmol), 6 mL DCM was added, and then the reaction solution was cooled to about −78° C. Diisobutyl aluminium hydride (DIBAL-H) (0.5 mL, 0.56 mmol, 1.2 mol/L) was slowly added dropwise, and then slowly warmed to room temperature and reacted for 3 hrs. The reaction was quenched with saturated ammonium chloride and extracted with DCM. The organic phase was washed with saturated aqueous NaCl solution, dried over anhydrous Na$_2$SO$_4$, and purified by column chromatography (PE/EA), to obtain 29 mg of Compound VII as a light yellow solid. Yield 83%.

Synthesis of Compound VIII

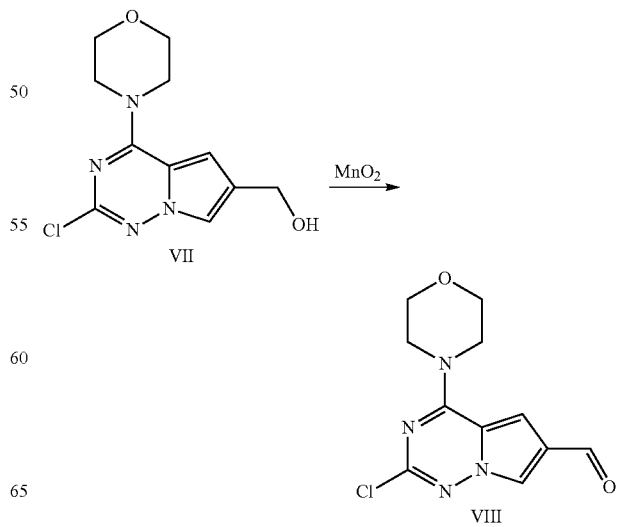

Compound VII (40 mg, 0.15 mmol) was added to 6 mL DCM, and then MnO$_2$ (103 mg, 1.2 mmol) was added, reacted at room temperature for 30 min, and filtered. The filtrate was dried over anhydrous Na$_2$SO$_4$ and then spun to dryness, to obtain 25 mg of Compound VIII as a light yellow solid. Yield 90%.

Example 2

Preparation of Compound I-1

Synthesis of Compound IX-1

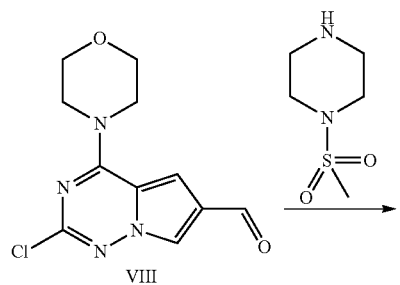

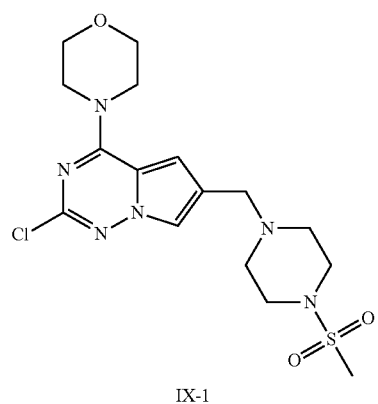

To Compound VIII (20 mg, 0.10 mmol), 5 mL 1,2-dichloroethane, 1-methansulfonyl piperazine (38 mg, 0.16 mmol), and triethyl amine (13 mg, 0.16 mmol) were added and stirred at room temperature for 30 min. Acetic acid (15 mg, 0.16 mmol) was added and reacted overnight at room temperature. Saturated NaHCO$_3$ was added and extraction was performed with DCM. The organic phase was washed with saturated aqueous NaCl solution, dried over anhydrous Na$_2$SO$_4$, and purified by column chromatography (MeOH:DCM), to obtain 27 mg of Compound IX-1 as a light yellow solid. Yield 86%. $^1$H NMR (400 MHz, DMSO-d$_6$) δ (ppm) 7.46 (m, 1H), 7.26 (s, 1H), 4.15 (m, 4H), 3.94 (m, 4H), 3.82 (s, 2H), 3.30 (m, 4H), 2.83 (s, 3H), 2.74 (m, 4H).

Synthesis of Compound I-1

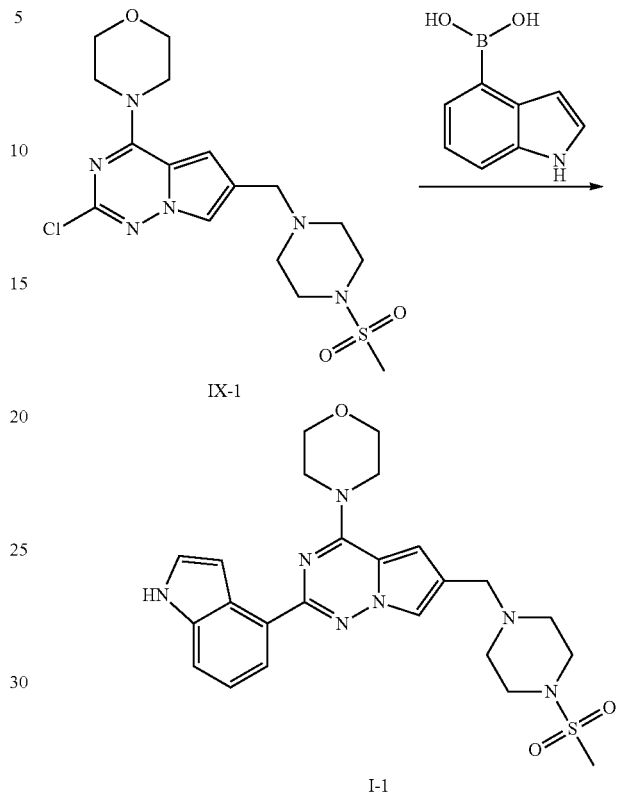

To Compound IX-1 (23 mg, 0.07 mmol), indol-4-boric acid (44 mg, 0.18 mmol), Na$_2$CO$_3$ (27 mg, 0.25 mmol), and PdCl$_2$ (PPh$_3$)$_2$ (6 mg, 0.007 mmol), 1.4 mL toluene, 0.7 mL ethanol and 0.5 mL water were added, and reacted for 20 min under microwave at 130° C. The reaction solution was cooled to room temperature, and extracted with EA. The organic phase was washed with saturated aqueous NaCl solution, dried over anhydrous Na$_2$SO$_4$, and purified by column chromatography (methanol MeOH:DCM), to obtain 10 mg of Compound I-1 as a light yellow solid. Yield 78%. Purity: 99%. $^1$H NMR (400 MHz, DMSO-d$_6$) δ (ppm) 8.47 (s, 1H), 8.18 (d, J=1.5 Hz, 1H), 7.70 (s, 1H), 7.57 (d, J=7.2 Hz, 1H), 7.72-7.33 (m, 2H), 6.66 (s, 1H), 4.15 (m, 4H), 3.94 (m, 4H), 3.62 (s, 2H), 3.30 (m, 4H), 3.10 (m, 4H), 2.83 (s, 3H), 2.62 (m, 4H); MS (ES+APCI) M+1=496.

Example 3

Preparation of Compound I-2

The title compound was synthesized following the process specifically shown in Example 2 with Compound IX-1 and indazol-4-boric acid as raw materials.

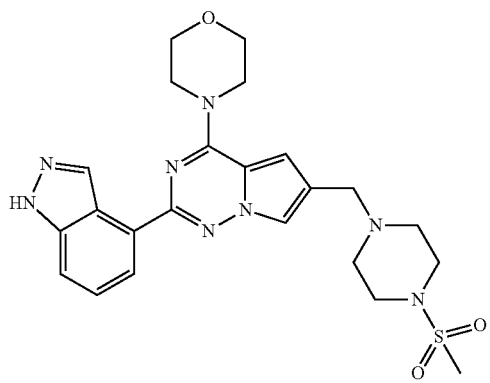

I-2

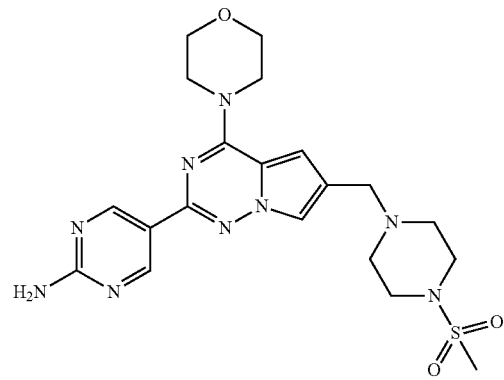

I-4

¹H NMR (400 MHz, DMSO-d₆) δ (ppm) 8.88 (s, 1H), 8.23 (d, J=7.1 Hz, 1H), 8.13 (d, J=5.5 Hz, 1H), 7.69 (d, J=8.3 Hz, 1H), 7.48 (m, 1H), 7.28 (s, 1H), 4.15 (m, 4H), 3.94 (m, 4H), 3.82 (s, 2H), 3.30 (m, 4H), 2.83 (s, 3H), 2.74 (m, 4H); MS (ES+APCI) M+1=497.

¹H NMR (400 MHz, DMSO-d₆) δ (ppm) 8.94 (s, 2H), 8.81 (s, 1H), 7.26 (s, 1H), 4.16 (m, 4H), 3.90 (m, 4H), 3.82 (s, 2H), 3.30 (m, 4H), 2.84 (s, 3H), 2.72 (m, 4H); MS (ES+APCI) M+1=474.

Example 4

Preparation of Compound I-3

The title compound was synthesized following the process specifically shown in Example 2 with Compound IX-1 and 7-azaindol-4-boric acid as raw materials.

Example 6

Preparation of Compound I-5

Synthesis of Compound X

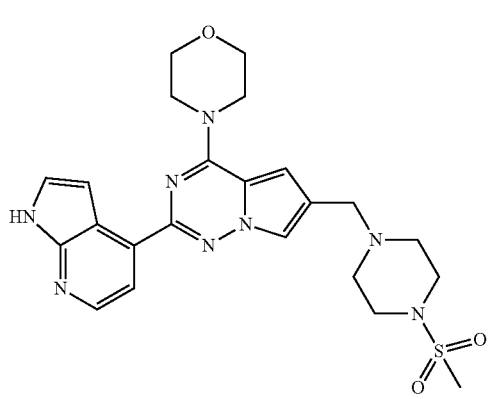

I-3

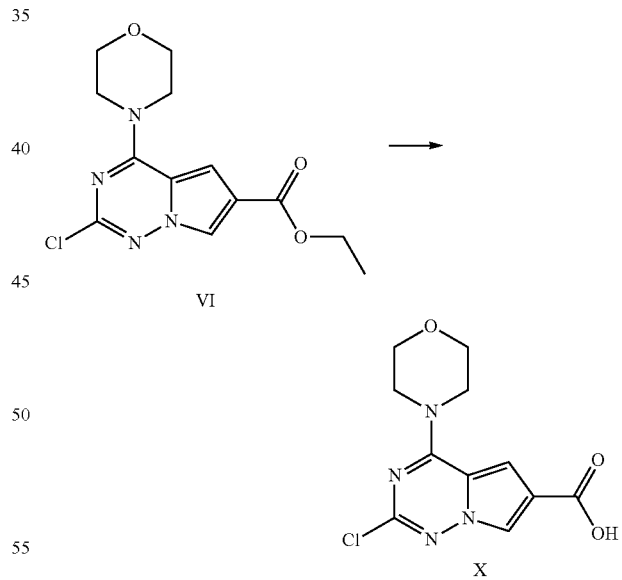

¹H NMR (400 MHz, DMSO-d₆) δ (ppm) 8.31 (d, J=5.0 Hz, 1H), 7.91 (d, J=5.0 Hz, 1H), 7.88 (d, J=1.1 Hz, 1H), 7.57 (t, 1H), 7.24 (t, 1H), 6.97 (d, J=1.1 Hz, 1H), 4.15 (m, 4H), 3.94 (m, 4H), 3.62 (s, 2H), 3.30 (m, 4H), 3.10 (m, 4H), 2.83 (s, 3H), 2.74 (m, 4H); MS (ES+APCI) M+1=497.

Example 5

Preparation of Compound I-4

The title compound was synthesized following the process specifically shown in Example 2 with Compound IX-1 and 2-aminopyrimidin-5-boric acid (which was synthesized following the method described in Chinese Patent No. CN102367260 A1) as raw materials.

To Compound VI (500 mg, 1.5 mmol), 6 mL methanol and 4 mL (1 M) NaOH solution were added, reacted under reflux for 24 hrs, and cooled to room temperature. Methanol was reduced, and the reaction solution was adjusted with 1 M hydrochloric acid to pH 5, and then extracted with DCM. The organic phase was washed with saturated aqueous NaCl solution, dried over anhydrous Na₂SO₄, and purified by column chromatography (PE/EA), to obtain 469 mg of Compound X as a light yellow solid. Yield 95%.

Synthesis of Compound XI

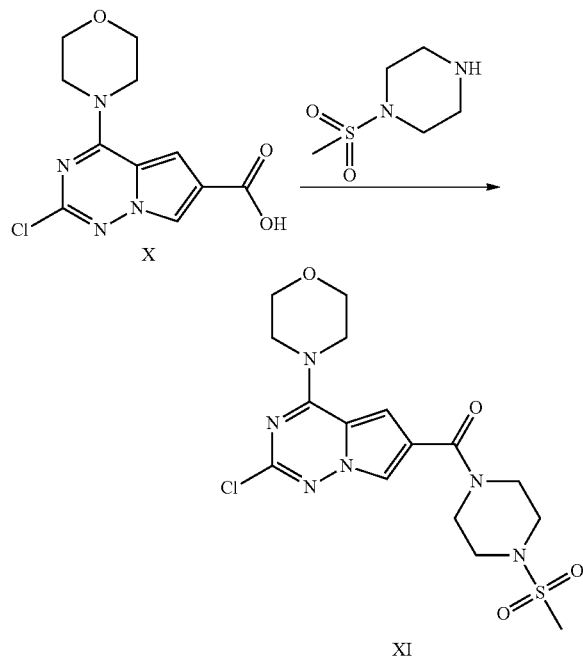

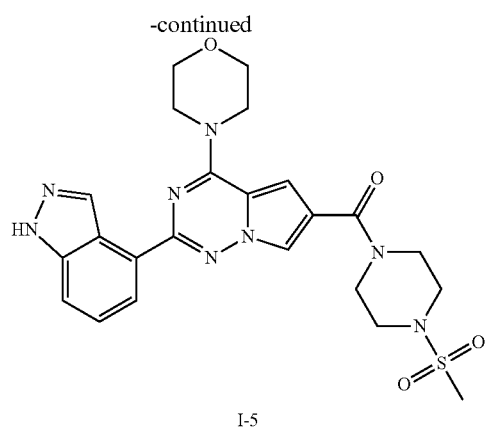

To Compound X (78 mg, 0.28 mmol), 6 mL DMF was added, and then 1-methansulfonyl piperazine (100 mg, 0.36 mmol), 1-ethyl-(3-dimethylaminopropyl)carbodiimide hydrochloride (EDC.HCl) (116 mg, 0.62 mmol), 1-hydroxybenzotriazole (HOBT) (42 mg, 0.28 mmol), and triethylamine (52 mg, 0.36 mmol) were added and then reacted overnight at room temperature. 10 mL water was added and extraction was performed with EA. The organic phase was washed with saturated aqueous NaCl solution, dried over anhydrous $Na_2SO_4$, spun to dryness, and purified by column chromatography, to obtain 43 mg of Compound XI as a white solid. Yield 75.5%. $^1$H NMR (400 MHz, $CDCl_3$) δ (ppm) 7.70 (d, J=1.6 Hz, 1H), 7.28 (d, J=1.6 Hz, 1H), 4.1 (m, 4H), 3.80-3.91 (m, 8H), 3.20 (m, 4H), 2.83 (s, 3H), MS Found $(M+H)^+$=429.8.

Synthesis of Compound I-5

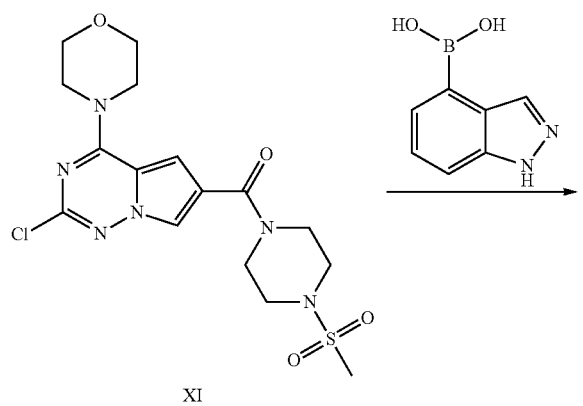

To Compound XI (82 mg, 0.2 mmol), indazol-4-boric acid (93 mg, 0.4 mmol), $Na_2CO_3$ (71 mg, 0.7 mmol), and $PdCl_2(PPh_3)_2$ (15 mg, 0.02 mmol), 1.4 mL toluene, 0.7 mL ethanol, and 0.5 mL water were added, and reacted for 30 min under microwave at 150° C. The reaction solution was cooled to room temperature, and extracted with EA. The organic phase was washed with saturated aqueous NaCl solution, dried over anhydrous $Na_2SO_4$, and purified by column chromatography (MeOH:DCM), to obtain 104 mg of Compound I-5 as a light yellow solid. Yield 85.5%. $^1$H NMR (400 MHz, DMSO-$d_6$) δ (ppm) 8.90 (s, 1H), 8.18 (d, J=7.1 Hz, 1H), 7.73 (m, 1H), 7.60 (m, 1H), 7.51 (d, J=7.3 Hz, 1H), 6.97 (s, 1H), 4.15 (m, 4H), 3.94 (m, 4H), 3.62 (s, 2H), 3.30 (m, 4H), 3.10 (m, 4H), 2.83 (s, 3H), 2.62 (m, 4H); MS (ES+APCI) M+1=498.

Example 7

Preparation of Compound I-6

Synthesis of Compound XII

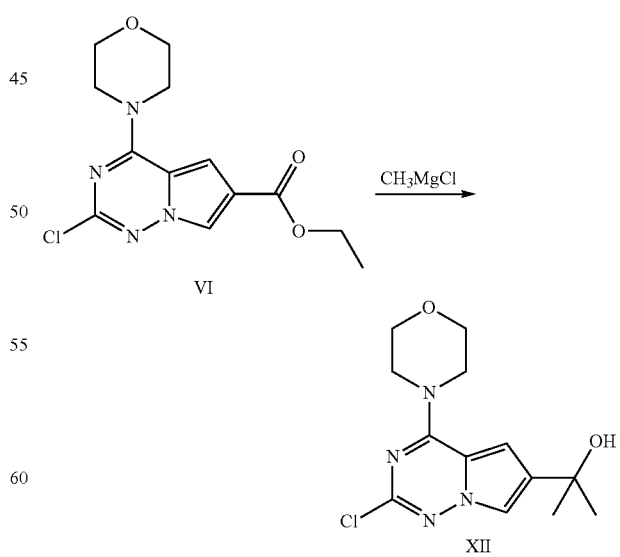

To Compound VI (20 mg, 0.10 mmol), 5 mL 1,2-dichloroethane, $CH_3MgCl$ (38 mg, 0.16 mmol), and triethylamine (13 mg, 0.16 mmol) were added, and stirred at room temperature for 30 min. Acetic acid (15 mg, 0.16 mmol) was added and reacted overnight at room temperature. Saturated NaHCO₃ was added, and extraction was performed with DCM. The organic phase was washed with saturated aqueous NaCl solution, dried over anhydrous Na₂SO₄, and purified by column chromatography (MeOH:DCM), to obtain 24 mg of Compound XII as a light yellow solid. Yield 77%. ¹H NMR (400 MHz, DMSO-d₆) δ (ppm): 8.23 (d, J=1.2 Hz, 1H), 7.18 (d, J=1.2 Hz, 1H), 4.15 (m, 4H), 3.94 (m, 4H), 2.08 (s, 6H); MS Found (M+H)⁺=296.6.

Synthesis of Compound I-6

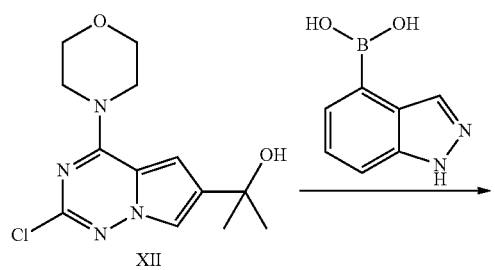

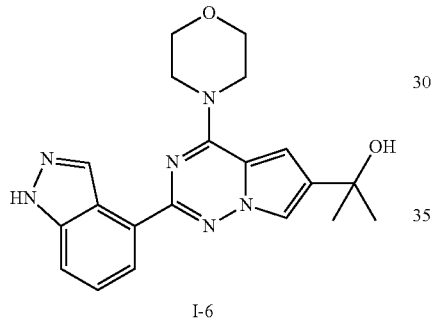

I-6

To Compound XII (30 mg, 0.07 mmol), indazol-4-boric acid (44 mg, 0.18 mmol), Na₂CO₃ (27 mg, 0.25 mmol), and PdCl₂(PPh₃)₂ (6 mg, 0.007 mmol), 1.4 mL toluene, 0.7 mL ethanol, and 0.5 mL water were added, and reacted for 25 min under microwave at 140° C. The reaction solution was cooled to room temperature, and extracted with EA. The organic phase was washed with saturated aqueous NaCl solution, dried over anhydrous Na₂SO₄, and purified by column chromatography (MeOH:DCM), to obtain 15 mg of Compound I-6 as a light yellow solid. Yield 80.5%. Purity: 99%. ¹H NMR (400 MHz, DMSO-d₆) δ (ppm) 8.79 (s, 1H), 8.13 (d, J=7.1 Hz, 1H), 7.78 (d, J=1.4 Hz, 1H), 7.69 (d, J=1 A Hz, 1H), 7.48 (m, 1H), 6.96 (d, J=1.4 Hz, 1H), 4.97 (s, 1H), 4.15 (m, 4H), 384 (m, 4H), 1.52 (s, 6H); MS (ES+APCI) M+1=379.

Example 8

Preparation of Compound I-7

Compound VIII and 1-ethansulfonylpiperazine, as raw materials were reacted, and then reacted with 2-aminopyrimidin-5-boric acid. The specific synthesis process was as shown in Example 2.

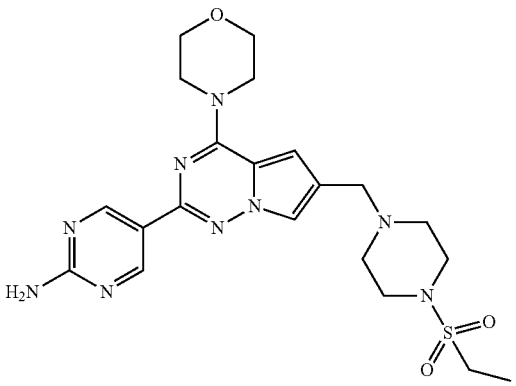

¹HNMR (400 MHz, DMSO-d₆) δ (ppm) 8.96 (s, 2H), 8.79 (s, 1H), 7.21 (s, 2H), 4.03 (q, 2H), 3.89-4.00 (m, 4H), 3.84 (s, 2H), 3.66-3.77 (m, 4H), 3.34-3.62 (m, 4H), 2.36-2.59 (m, 4H), 1.55 (t, 3H); MS (ES+APCI) M+1=488.

Example 9

Preparation of Compound I-8

Compound VIII and 1-acetylpiperazine, as raw materials were reacted, and then reacted with 2-aminopyrimidin-5-boric acid. The specific synthesis process was as shown in Example 2.

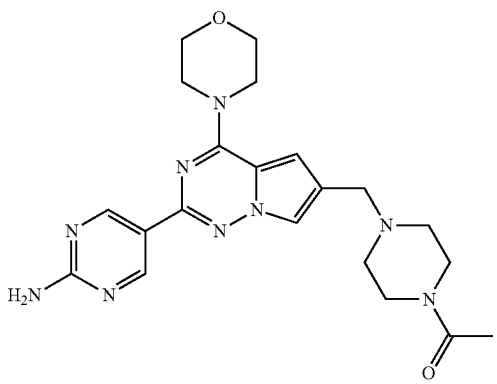

¹HNMR (400 MHz, DMSO-d₆) δ (ppm) 8.94 (s, 2H), 8.80 (s, 1H), 7.29 (s, 1H), 3.89-4.00 (m, 4H), 3.66-3.77 (m, 4H), 3.34-3.62 (m, 4H), 2.36-2.59 (m, 4H), 1.90 (s, 3H); MS (ES+APCI) M+1=438.

Example 10

Preparation of Compound I-9

Compound VIII and 1-cyclopropionylpiperazine, as raw materials were reacted, and then reacted with 2-aminopyrimidin-5-boric acid. The specific synthesis process was as shown in Example 2.

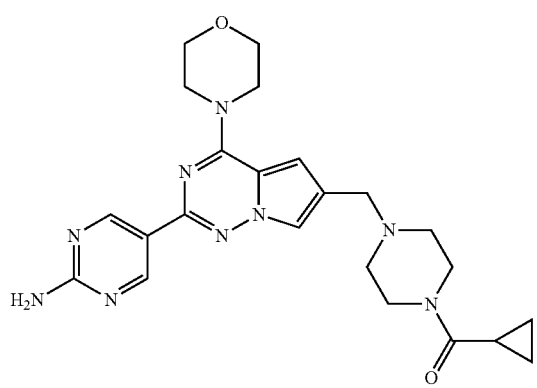

¹HNMR (400 MHz, DMSO-d₆) δ (ppm) 8.93 (s, 2H), 8.23 (s, 1H), 7.29 (s, 1H), 3.85-3.96 (m, 4H), 3.78-3.80 (m, 6H), 3.63-3.72 (m, 4H), 3.35-3.63 (m, 4H), 1.33 (m, 1H), 0.95 (m, 2H), 0.71 (m, 2H); MS (ES+APCI) M+1=464.

Example 11

Preparation of Compound I-10

Synthesis of Compound XV

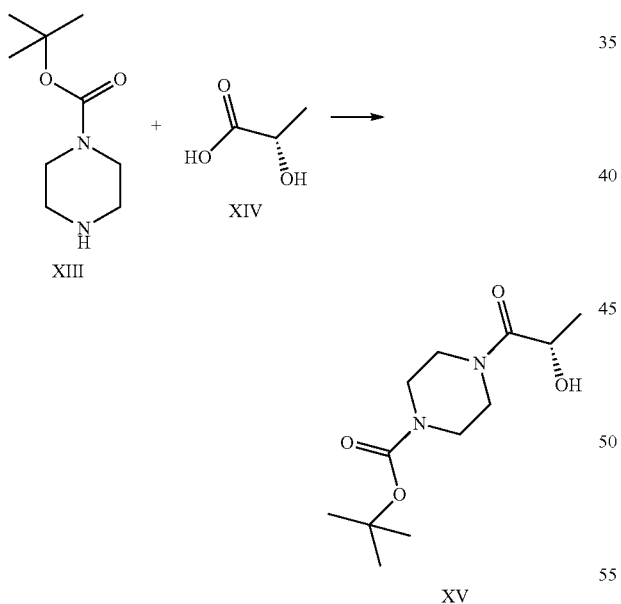

Compound XIV (180 mg, 2 mmol), 2-(7-azobenzotriazole)-N,N,N',N'-tetramethyluronium hexafluorophosphate (HATU) (570 mg, 1.5 mmol), DIPEA (194 mg, 1.5 mmol), and Compound XIII (186 mg, 1 mmol) were added to 2 mL DMF, and stirred at room temperature for 0.5 h. After the reaction was complete, EA (15 mL) was added. The organic phase was washed with water and then saline, dried, and concentrated, to obtain 200 mg of Compound XV as a white solid. Yield: 77.5%.

Synthesis of Compound XVI

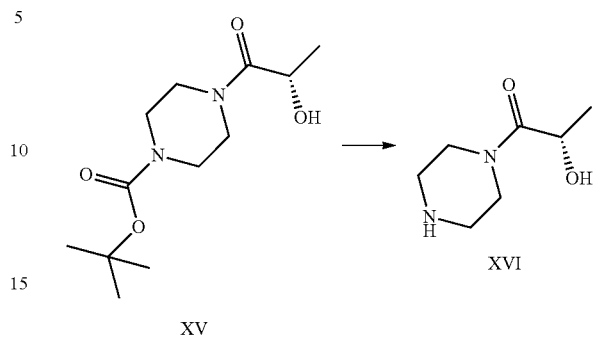

Compound XV (200 mg, 0.77 mmol) was added to 5 mL DCM, and then trifluoroacetic acid (TFA) (500 mg, 1 mmol) was added, stirred at room temperature for 0.5 hr, and concentrated to obtain 85 mg of Compound XVI as colorless oil. Yield 97%.

Synthesis of Compound I-10

Compound VIII and Compound XVI ((S)-1-(2-hydroxypropionyl)piperazine), as raw materials, were reacted and then reacted with 2-aminopyrimidin-5-boric acid. The specific synthesis process was as shown in Example 2.

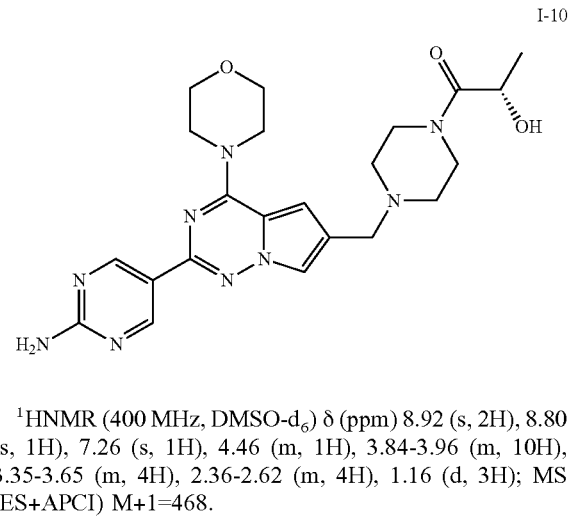

¹HNMR (400 MHz, DMSO-d₆) δ (ppm) 8.92 (s, 2H), 8.80 (s, 1H), 7.26 (s, 1H), 4.46 (m, 1H), 3.84-3.96 (m, 10H), 3.35-3.65 (m, 4H), 2.36-2.62 (m, 4H), 1.16 (d, 3H); MS (ES+APCI) M+1=468.

Example 12

Preparation of Compound I-11

Compound VIII and (R)-1-(2-hydroxypropionyl)piperazine (which was synthesized with Compound XIII and D-lactic acid, through a process as described for Compound XVI in Example 11) as raw materials, were reacted, and then reacted with 2-aminopyrimidin-5-boric acid. The specific synthesis process was as shown in Example 2.

I-11

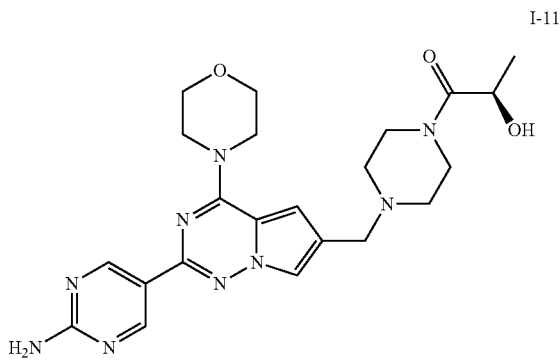 [SMILES: C[C@@H](O)C(=O)N1CCN(Cc2cc3c(N4CCOCC4)nc(-c4cnc(N)nc4)nn3c2)CC1]

$^1$HNMR (400 MHz, DMSO-d$_6$) δ (ppm) 8.95 (s, 2H), 8.81 (s, 1H), 7.28 (s, 1H), 4.48 (m, 1H), 3.86-3.98 (m, 6H), 3.70-3.78 (m, 4H), 3.38-3.68 (m, 4H), 2.38-2.62 (m, 4H), 1.18 (d, 3H); MS (ES+APCI) M+1=468.

What is claimed is:

1. A compound of structural Formula (I), or a pharmaceutically acceptable salt thereof:

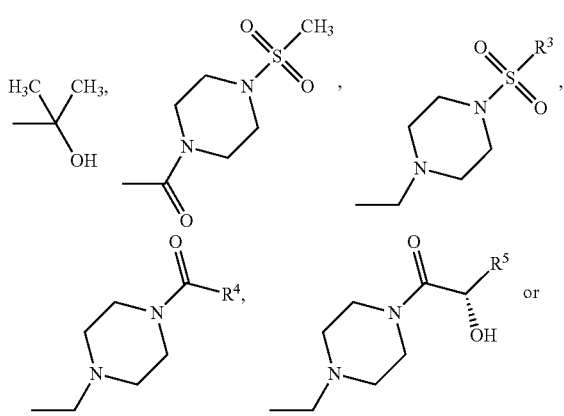

wherein R$^1$ represents indolyl, indazolyl, azaindolyl, or aminopyrimidinyl;
R$^2$ represents

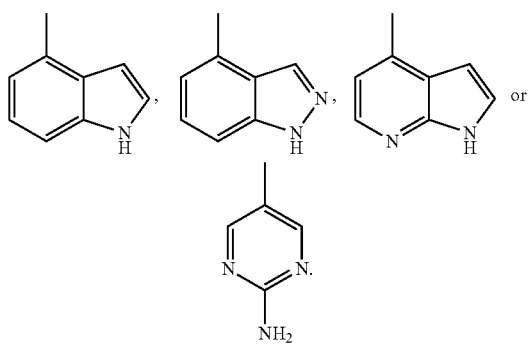

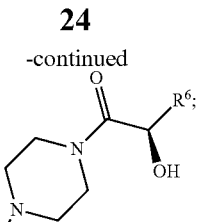

R$^3$ represents C$_1$-C$_6$ alkyl, R$^4$ represents C$_1$-C$_6$ alkyl, and R$^5$ represents C$_1$-C$_6$ alkyl.

2. The compound of claim 1 or a pharmaceutically acceptable salt thereof, wherein R$^1$ represents:

3. The compound of claim 1 or a pharmaceutically acceptable salt thereof, wherein R$^3$ represents methyl or ethyl.

4. The compound of claim 1 or a pharmaceutically acceptable salt thereof, wherein R$^4$ represents methyl or cyclopropyl.

5. The compound of claim 1 or a pharmaceutically acceptable salt thereof, wherein R$^5$ represents methyl.

6. The compound of claim 1 or a pharmaceutically acceptable salt thereof, wherein the pharmaceutically acceptable salt is a salt of the compound of claim 1 with arginine, hydrochloric acid, sulfuric acid, phosphoric acid, maleic acid, fumaric acid, citric acid, methansulfonic acid, p-toluene sulfonic acid, or tartaric acid.

7. A pharmaceutical composition, comprising the compound of claim 1 or a pharmaceutically acceptable salt thereof, and a pharmaceutically acceptable carrier.

8. A method of treating a tumor comprising administering a compound according to claim 1 to a subject in need thereof, wherein the tumor is selected from the group consisting of gastric cancer, lung cancer, liver cancer, breast cancer, colon cancer, and prostatic cancer.

9. A method of treating a tumor comprising administering a composition according to claim 7 to a subject in need thereof, wherein the tumor is selected from the group consisting of gastric cancer, lung cancer, liver cancer, breast cancer, colon cancer, and prostatic cancer.

* * * * *